United States Patent [19]

Emery et al.

[11] Patent Number: 5,160,319
[45] Date of Patent: Nov. 3, 1992

[54] DUAL-LUMEN OOCYTE ASPIRATION NEEDLE

[75] Inventors: Jamie Emery, Canyon Country; Horace Montgomery, Laguna Beach, both of Calif.

[73] Assignee: Baxter International Inc., Deerfield, Ill.

[21] Appl. No.: 780,592

[22] Filed: Oct. 23, 1991

[51] Int. Cl.$^5$ .............................................. A61M 1/00
[52] U.S. Cl. ........................................ 604/27; 604/35; 604/44; 604/55; 604/158
[58] Field of Search ............... 604/27, 28, 43, 44, 604/45, 51, 52, 53, 55, 158-169, 272, 187, 188, 35, 36, 902

[56] References Cited

U.S. PATENT DOCUMENTS

| | | |
|---|---|---|
| 3,007,471 | 11/1961 | McClure, Jr. . |
| 3,610,226 | 10/1971 | Albisser . |
| 4,224,943 | 9/1980 | Johnson et al. ................ 604/44 |
| 4,299,217 | 11/1981 | Sagae et al. .................... 604/44 |
| 4,356,828 | 11/1982 | Jamshidi . |
| 4,493,694 | 1/1985 | Wuchinich . |
| 4,533,345 | 8/1985 | Louw . |
| 4,553,957 | 11/1985 | Williams et al. . |
| 4,573,979 | 3/1986 | Blake . |
| 4,685,904 | 8/1987 | Krebs . |
| 4,731,052 | 3/1988 | Seitz, Jr. . |
| 4,904,238 | 2/1990 | Williams . |
| 4,986,279 | 1/1991 | O'Neill . |
| 4,995,865 | 2/1991 | Gahara et al. ................. 604/53 |

FOREIGN PATENT DOCUMENTS 0391511 10/1990 European Pat. Off. .

Primary Examiner—John D. Yasko
Attorney, Agent, or Firm—Kay H. Pierce; Paul C. Flattery

[57] ABSTRACT

A dual-lumen oocyte collection device is described. The device is unique in that it includes parallel cannulas which extend axially outward from a proximal end of a hub. The device is also unique in that it further includes a finger depression on the hub. This depression located on the hub directly corresponds to an elongated beveled point of a cannula that extends from a distal end of the hub. The unique parallel cannulas and the finger depression allow medical personnel to evenly rotate and accurately orientate the beveled tip of the device to puncture a follicle on an ovary with minimal trauma prior to collecting an oocyte.

7 Claims, 3 Drawing Sheets

DUAL-LUMEN OOCYTE ASPIRATION NEEDLE

BACKGROUND OF THE INVENTION

1. Field of the Invention

The present invention relates to devices for use in collecting an oocyte from the ovary of a patient for use in a surgically-assisted reproduction procedure, and more specifically relates to a dual-lumen oocyte collection device.

2. Discussion of the Prior Art

Surgically-assisted reproduction techniques such as in vitro fertilization (IVF) and gamete intrafallopian transfer (GIFT) have become widely accepted clinical methods for the treatment of infertility. During the past several years, advances in laboratory techniques and physician expertise have significantly improved the chances for a successful pregnancy.

IVF involves the fertilization of a female oocyte or egg in vitro (outside of the womb). With GIFT, fertilization occurs in vivo (within the womb). Regardless of which of these fertilization methods is employed, oocytes are retrieved from ovarian follicles (sac-like structures on the ovaries that contain the oocytes) by either a laparoscopic or transvaginal procedure using an aspiration needle.

During an oocyte retrieval procedure, a relatively long aspiration needle is either vaginally or abdominally inserted into a patient so that the distal end of the needle is in contact with a patient's ovary. The objective is to puncture an individual follicle on the ovary and withdraw a single oocyte up through the needle. Generally, the proximal end of the needle is connected to flexible tubing which is, in turn, connected to both a test tube and a vacuum source. The vacuum source provides suction through both the tubing and the needle to allow aspiration of the oocyte from the follicle.

As follicular fluid is aspirated, it travels through the needle and tubing into the test tube. The contents of the test tube are periodically examined microscopically to determine whether an oocyte is present. In some instances, the oocyte may become lodged in the needle or in the follicle and is not easily aspirated. In such instances, it may be necessary to irrigate the follicle and needle to dislodge the oocyte and allow aspiration of the oocyte into the test tube.

Two different needle styles are currently used for oocyte retrievals. One needle style is a single-lumen device. This style requires that any irrigation that is performed be conducted through the same fluid path (or lumen) that is used for aspiration. In such instances, if an oocyte is lodged in the fluid path, the oocyte may be actually flushed back into the follicle during the irrigation procedure. Therefore, the use of a single-lumen device may create the potential of losing the oocyte during the irrigation procedure. Accordingly, some physicians prefer the use of a dual-lumen device for oocyte collection procedures. A dual-lumen device has a first fluid path, or lumen, for aspiration and a second fluid path for irrigation. The use of separate paths thereby reduces the possibility of flushing an oocyte out of the aspiration path during an irrigation procedure.

As discussed above, each oocyte is located in a fluid-filled sac or follicle. Before an oocyte can be retrieved, a physician needs to be able to accurately puncture each sac prior to retrieval without damaging or losing the oocyte. In order to cleanly puncture the sac, all oocyte collection devices include a cannula having a sharpened beveled tip. Ideally, the tip is gently inserted into the follicle to puncture the sac and release the oocyte.

Obviously, it is very important that as the tip is rotated the physician knows the orientation and location of the tip. Therefore, a need exists to provide a means for easily determining the orientation of the beveled tip and to provide a means for allowing a physician to evenly rotate the tip. Unfortunately, many oocyte collection devices contain a cannula which extends radially outwardly. Generally, any cannula which extends radially outward may make it difficult for a physician to evenly rotate the device without traumatizing the patient's ovary. If a patient's ovary is traumatized, it may further complicate the patient's ability to conceive. Thus, it is critical to evenly rotate an oocyte collection device and, thus, be able to retrieve an oocyte without traumatizing a patient's ovary.

SUMMARY OF THE INVENTION

A device is described for retrieving human oocytes from a female ovary. The device includes a first hub having distal and proximal ends. The first hub includes a central channel which extends from its distal to its proximal end.

The device also includes a second hub having distal and proximal ends. The distal end of the second hub is connected to the proximal end of the first hub. The second hub has first and second channels which extend from its distal to its proximal ends. The first and second channels are in fluid communication with the central channel in the first hub.

The device also includes an outer cannula having inner and outer walls. The proximal end of the outer cannula is attached to the distal end of the first hub. The inner wall of the outer cannula forms a fluid path. This fluid path is in fluid communication with the central channel of the first hub.

The device still further includes an integral aspiration cannula which has distal and proximal ends and which also has inner and outer walls. The distal end of the aspiration cannula is attached to the proximal end of the second hub. Portions of the integral aspiration cannula extend: (1) through the first channel of the second hub; (2) through the central channel of the first hub; and (3) substantially through the length of the outer cannula. The portion of the aspiration cannula which extends substantially through the length of the outer cannula is located within, and is substantially parallel to, the inner wall of the outer cannula.

The aspiration cannula has another portion which extends outwardly from the proximal end of the second hub. The inner wall of the aspiration cannula forms an inner aspiration channel that is used to withdraw an oocyte from the distal end of the outer cannula through the first and second hubs.

The device also includes a side cannula which is attached to the proximal end of the second hub. A portion of the side cannula extends through the second channel of the second hub and is in fluid communication with the central channel of the first hub. The side cannula, the outer wall of the aspiration cannula, and the inner wall of the outer cannula form an outer irrigation channel. The outer irrigation channel extends from the proximal end of the side cannula to the distal end of the outer cannula.

The side cannula has a portion which extends axially outward from the proximal end of the second hub. The portions of the aspiration and side cannulas which extend axially outward from the proximal end of the second hub are parallel to one another to allow the device to be more easily, and evenly, rotated.

The device still further includes a collection tube which has a distal end that is attached to the proximal end of the aspiration cannula. A proximal end of the collection tube is attached to a test tube and to a vacuum source. The purpose of the collection tube is to provide means for applying a vacuum to the aspiration channel and to transfer an oocyte from the aspiration channel to the test tube.

Finally, the device includes an irrigation tube which has a distal end that is attached to the proximal end of the side cannula. Irrigation medium may be injected through the irrigation tube into the irrigation channel as required in order to flush an oocyte which may be lodged either in a patient's follicle or in the aspiration channel.

In the preferred embodiment, the device includes a beveled point at the distal end of the outer cannula and a depressed area on the first hub which corresponds to the beveled point. This depressed area can be used to orient the beveled point as the beveled point is evenly rotated for the purpose of puncturing a patient's follicle prior to oocyte retrieval.

DESCRIPTION OF THE PREFERRED EMBODIMENT

Figure 1:
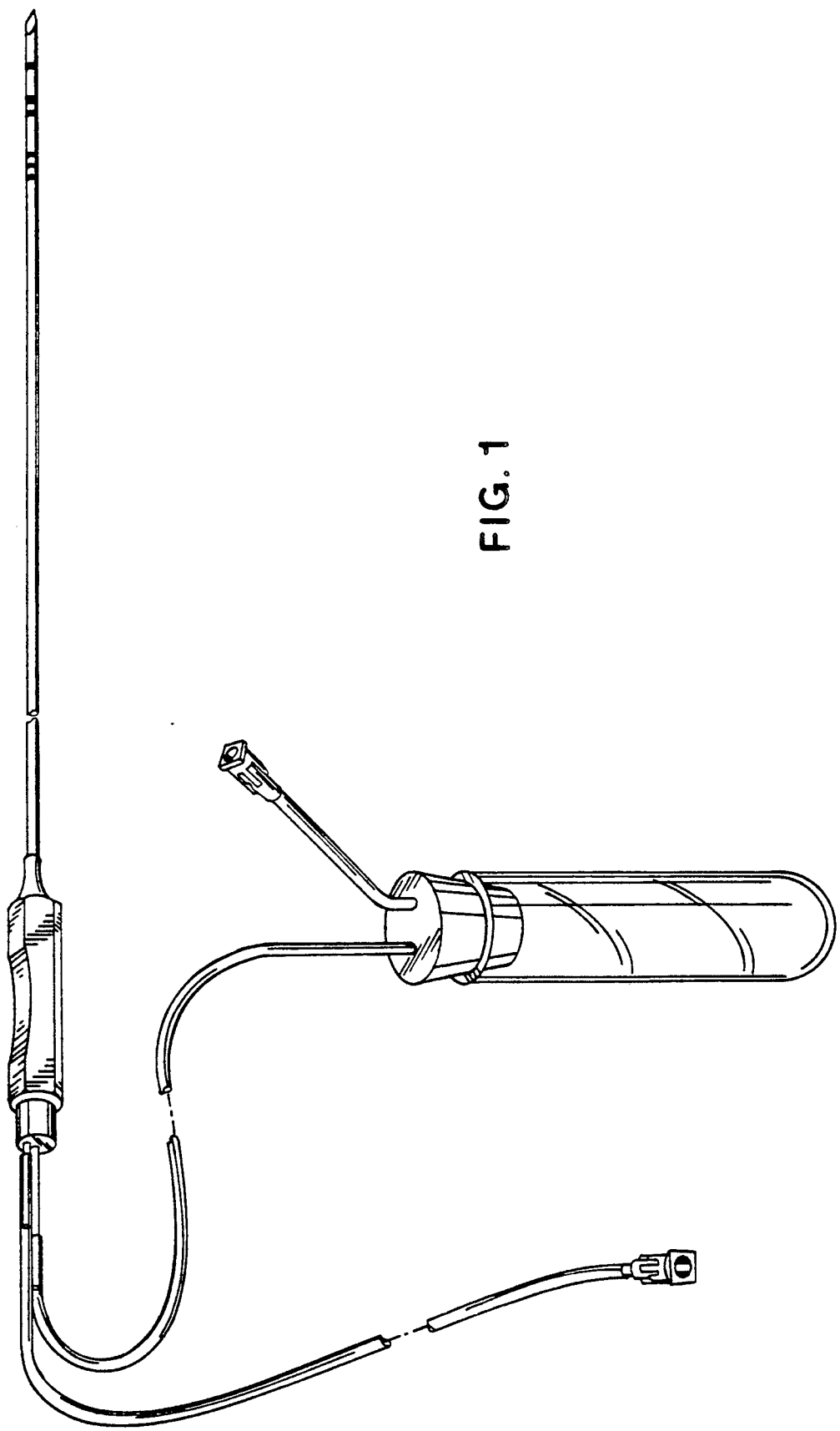
FIG. 1 is a perspective view of the preferred embodiment of the invention.
Figure 2:
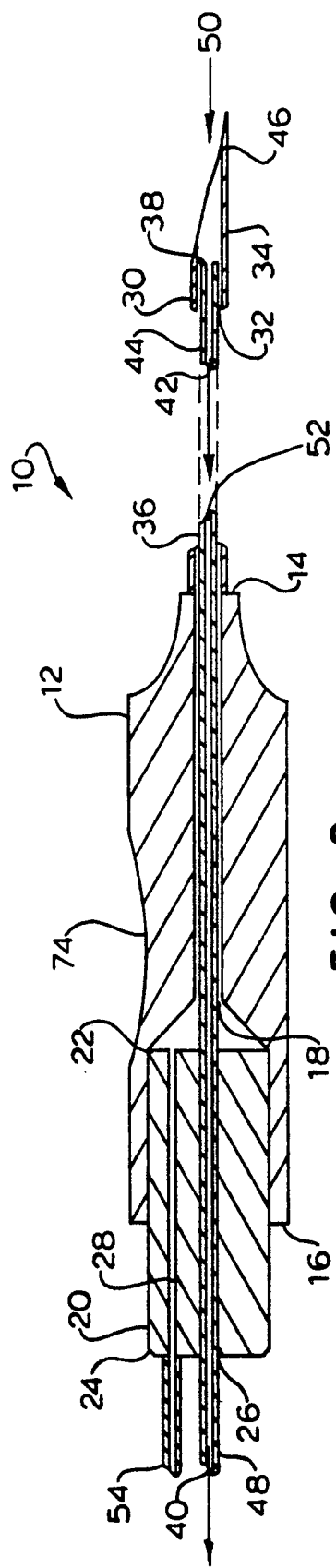
FIG. 2 is a cross-sectional view of the preferred embodiment illustrating the fluid aspiration channel.

Refer now to FIG. 1 which is an exploded perspective view of the preferred embodiment of the oocyte collection device 10. The device includes a first hub 12 having distal and proximal ends 14, 16. The first hub 12 has a central channel 18 extending therethrough (FIG. 2). The channel 18 extends from the distal end 14 to the proximal end 16.

The device 10 also includes a second hub 20 having distal and proximal ends 22, 24. The second hub 20 has first and second channels 26, 28 which extend from the distal end 22 to the proximal end 24 of the second hub 20. The first and second channels 26 and 28 are in fluid communication with the central channel 18 in the first hub 12 at the proximal end 16 of the first hub.

The device 10 also includes an outer cannula 30 having inner and outer walls 32, 34. The outer cannula 30 is attached to the distal end 14 of the first hub 12. The outer cannula 30 is in fluid communication with the central channel 18 of the first hub 12.

The device 10 still further includes an integral aspiration cannula 36 that has distal and proximal ends 38, 40. The aspiration cannula 36 also includes inner and outer walls 42, 44. The aspiration cannula 36 is attached to the proximal end 24 of the second hub 20. The aspiration cannula 36 extends through the first channel 26 of the second hub 20. The aspiration cannula 36 also extends through the central channel 18 of the first hub 12. Finally, the aspiration cannula 36 extends through substantially the entire length of the outer cannula 30 so that the outer wall 44 of the aspiration cannula 36 is located within and is substantially parallel with the inner wall 32 of the outer cannula 30. Thus, an aspiration flow channel 50 is created from the distal end 46 of the outer cannula 30 through the inner wall 42 of the aspiration cannula 36.

The aspiration cannula 36 also has a portion 48 which extends axially outward from the proximal end 24 of the second hub 20. The inner wall 42 of the aspiration cannula 36 forms an inner aspiration channel 52 to withdraw an oocyte from the distal end 46 of the outer cannula 30 through the first and second hubs 12, 20.

Figure 3:
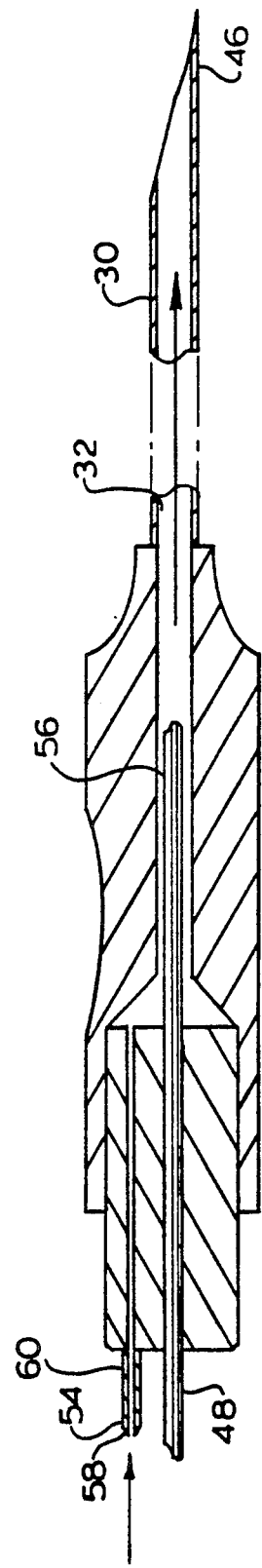
FIG. 3 is a cross-sectional view of the preferred embodiment illustrating the fluid irrigation channel.
Figure 4:
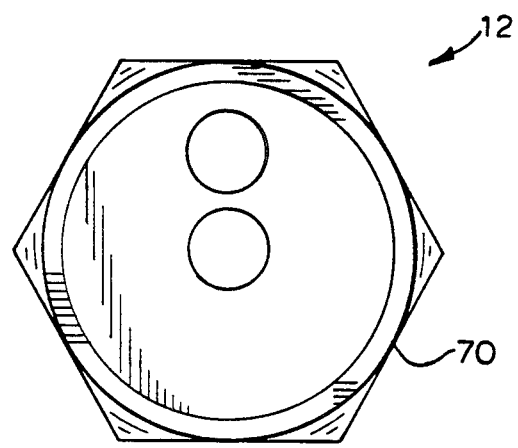
FIG. 4 is a cross-sectional view of the second hub of the preferred embodiment of the invention.

A side cannula 54 is attached to the proximal end 24 of the second hub 20. The side cannula 54 extends through the second channel 28 of the second hub 20. The side cannula 54 is in fluid communication with the central channel 18 of the first hub 12. The side cannula 54, the outer wall 44 of the aspiration cannula 36, and the inner wall 32 of the outer cannula 30 form an outer irrigation channel 56 which is illustrated in FIG. 3. The outer irrigation channel 56 extends from the proximal end 58 of the side cannula 54 to the distal end 46 of the outer cannula 30.

The side cannula 54 has a portion 60 which extends axially outward from the proximal end 24 of the second hub 20 so that the portions of the aspiration and side cannulas 48, 60 that extend axially outward from the proximal end 24 of the second hub 20 are parallel to one another. This is important because it allows medical personnel to evenly rotate the device 10 during a medical procedure. If the side cannula 54 extends radially outward from the second hub 20, the side cannula 54 would inhibit even rotation of the device 10.

In the preferred embodiment, a collection tube 62 is attached to the proximal end 40 of the aspiration cannula 36. A vacuum source (not shown) may be attached to the collection tube 62 to provide a vacuum to the aspiration channel 52. The vacuum provides a means for withdrawing the oocyte from a patient's follicle and depositing the oocyte in a test tube 64 attached to the collection tube 62.

An irrigation tube 66 is attached to the proximal end 58 of the side cannula 54 to provide an irrigation medium to the irrigation channel 56.

Figure 5:
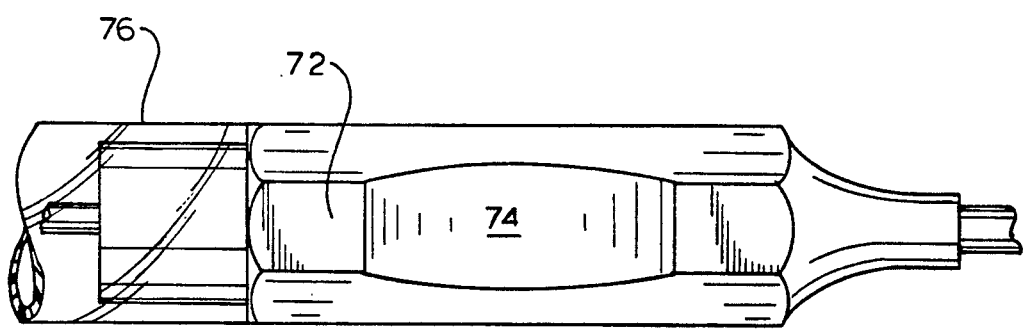
FIG. 5 is a side view of the first hub of the preferred embodiment.

In the preferred embodiment, the distal end 46 of the outer cannula 30 is provided with a sharpened beveled point 68 that can be used for penetration purposes. The first hub 12 is provided with multiple flat outer surfaces 70 which form a polygon (FIG. 5). In the preferred embodiment, the polygon is in the form of a hexagon.

In the preferred embodiment, one of the flat surfaces 72 includes a depressed area 74 which corresponds to the sharpened beveled point 68. By having a depressed area 74 on the first hub 12 which corresponds to the beveled point 68, a physician is able to precisely determine the orientation of the beveled point 68. Since the needle tip frequently appears as a dotted line on an ultrasound screen, the fact that the depressed area 74 is aligned with the tip of the sharpened beveled point 68 allows a physician to accurately determine the actual location and orientation of the point 68. Therefore, the physician can evenly rotate the beveled point 68 around the inside of a patient's follicle to puncture the follicle and release an oocyte.

In the preferred embodiment, a sleeve 76 is also provided which extends from the proximal end 24 of the second hub 20 to the collection and irrigation tubes 62, 66. The sleeve 76 surrounds the portions 60, 48 of the side and aspiration cannulas 54, 36 which extend axially outward from the proximal end 24 of the second hub 20. The sleeve 76 prevents the collection and irrigation tubes 62, 66 from collapsing at the proximal ends 58, 40 of the side and aspiration cannulas 54, 36.

In the preferred embodiment, the side and aspiration cannulas 54, 36 are formed of 304 grade stainless steel. The first and second hubs 12, 20 are formed of 303 grade stainless steel. The collection tube 62 and irrigation tube 66 are formed of a polymeric material. In the preferred embodiment, the polymeric material is polyethylene.

The device is assembled by first assembling the outer cannula 30 to the distal end 14 of the first hub 12 using an adhesive. Next, the side cannula 54 is assembled to the proximal end 24 of the second hub 20. The first and second hubs 12, 20 are then mechanically swaged together. The aspiration cannula 36 is inserted into the proximal end 24 of the second hub 20 and threaded through the entire length of the central channel 18 of the first hub 12 and substantially the entire length of the inner wall 32 of the outer cannula 30.

Then the collection tubes 62 and irrigation tubes 66 are assembled to the proximal end 40 of the aspiration cannula 36 and the proximal end 58 of the side cannula 54. The sleeve 76 is then placed over the junction of the collection tube 62, irrigation tube 66 and the proximal ends 40, 58 of the aspiration cannula 36 and the side cannula 54.

During on oocyte retrieval procedure, the distal end 46 of the outer cannula 30 is inserted into the patient's pelvic cavity and directed to the ovarian follicle using either laparoscopic or ultrasound guidance. The cannula can be inserted transabdominally using a laparoscope for visualization or transvaginally under ultrasound guidance. Once it has been determined that the distal end 46 of the outer cannula 30 is located in the area of a follicle, the beveled point 68 of the device 10 is gently inserted into the follicle. Immediately after the distal end 46 of the outer cannula 30 enters the follicle, a vacuum is applied to the aspiration channel 52 to aspirate the oocyte and any follicular fluid. During the aspiration procedure, the device 10 is gently rotated so that the beveled point 68 gently scrapes the internal follicle wall to dislodge the oocyte. This rotation is called intrafollicular curettage. Since it is important not to damage any adjacent follicles which may contain other oocytes and since it is important not to traumatize the patient's ovary, it is critical that this rotation procedure be performed very evenly. Therefore, it is highly advantageous to provide a device 10 in which the location of the beveled point 68 can be accurately determined. The preferred embodiment of the subject invention achieves this goal by having a depressed area 74 on the first hub 12 which directly corresponds to the orientation of the beveled point 68. The orientation of the beveled point corresponding to the depressed area allows the physician to accurately determine the actual location and orientation of the point and estimate the depth of needle penetration. Another goal is to provide a device which can be evenly rotated. This goal is accomplished by providing a hub having a hexagonal shape that allows a "rolling" motion between the fingertips. This goal is also accomplished by providing a side cannula 54 and an aspiration cannula 36 which extend axially outward from the proximal end 24 of the second hub 20, thereby eliminating any projections from the side 78 of the second hub 20.

While the invention has been described in detail and with reference to specific embodiments thereof, it will be apparent to those skilled in the art that various changes and modifications can be made therein without departing from the spirit and scope of the invention.

We claim:

1. A device for retrieving human oocytes from a female ovary, comprising:
   (a) a first hub having distal and proximal ends, said first hub having a central channel extending from said distal to said proximal end;
   (b) a second hub having distal and proximal ends, said second hub having first and second channels extending from said distal to said proximal ends, said first and second channels being in fluid communication with said central channel in said first hub at said proximal end of said first hub;
   (c) an outer cannula having inner and outer walls, said outer cannula being attached to said distal end of said first hub, said outer cannula being in fluid communication with said central channel of said first hub;
   (d) an aspiration cannula having distal and proximal ends and having inner and outer walls, said aspiration cannula being attached to said proximal end of said second hub, said aspiration cannula extending through
   said first channel of said second hub,
   said central channel of said first hub, and
   substantially through the length of said outer cannula so that said outer wall of said aspiration cannula is located within and is substantially parallel with said inner wall of said outer cannula
   said aspiration cannula also having a portion extending axially outward from said proximal end of said second hub, said inner wall of said aspiration cannula forming an inner aspiration channel to withdraw an oocyte from said distal end of said outer cannula through said first and second hubs;
   (e) a side cannula attached to said proximal end of said second hub, said side cannula extending through said second channel of said second hub and being in fluid communication with said central channel of said first hub, said side cannula, said outer wall of said aspiration cannula and said inner wall of said outer cannula forming an outer irrigation channel which extends from said proximal end of said side cannula to said distal end of said outer cannula;
   (f) said side cannula having a portion extending axially outward from said proximal end of said second hub so that said portions of said aspiration and side cannulas that extend axially outward from said proximal end of said second hub are parallel to one another;
   (g) a collection tube attached to said proximal end of said aspiration cannula to provide a vacuum to said aspiration channel and to receive an oocyte from said aspiration channel; and
   (h) an irrigation tube attached to said proximal end of said side cannula to provide irrigation medium to said irrigation channel.

2. A device as recited in claim 1 wherein said distal end of said outer cannula further includes a sharpened beveled point for penetration purposes and said first hub further includes multiple flat outer surfaces which form a polygon in which one flat surface has a depressed area which corresponds to said beveled point to allow medical personnel to orient said beveled point and to provide for ease of rotation of said device.

3. A device as recited in claim 1 further comprising:
a sleeve extending from said proximal end of said second hub to said collection and irrigation tubes and surrounding said portions of said side and aspiration cannulas that extend axially outward from said proximal end of said second hub to prevent said collection and irrigation tubes from collapsing at said proximal end of said side and aspiration cannulas.

4. A device as recited in claim 2 wherein said multiple flat outer surfaces form a hexagon.

5. A device as recited in claim 1 wherein said first hub, said second hub, said outer cannula, said aspiration cannula and side cannula are formed of stainless steel.

6. A device as recited in claim 1 wherein said collection and irrigation tubes are formed of a substantially transparent material to allow visualization during retrieval of an oocyte.

7. A device as recited in claim 3 wherein said sleeve and said collection and irrigation tubes are all formed of a flexible polymeric material.

* * * * *